United States Patent [19]
Jackson et al.

[11] Patent Number: 5,578,091
[45] Date of Patent: Nov. 26, 1996

[54] CHEMICAL COMPOSITIONS AND THEIR USE AS FUEL ADDITIVES

[75] Inventors: Graham Jackson, Reading; Rodger F. Andrews, Didcot, both of United Kingdom

[73] Assignee: Exxon Chemical Patents Inc., Linden, N.J.

[21] Appl. No.: 937,906

[22] PCT Filed: Apr. 19, 1991

[86] PCT No.: PCT/GB91/00623

§ 371 Date: Oct. 13, 1992

§ 102(e) Date: Oct. 13, 1992

[87] PCT Pub. No.: WO91/16297

PCT Pub. Date: Oct. 31, 1991

[30]  Foreign Application Priority Data

Apr. 19, 1990 [GB] United Kingdom ............... 9008811

[51] Int. Cl.$^6$ ...................................................... C10L 1/22
[52] U.S. Cl. .................. 44/399; 44/408; 44/413
[58] Field of Search .................... 44/399, 408, 409, 44/410, 413, 414, 422; C10L 1/22

[56]  References Cited

U.S. PATENT DOCUMENTS

| | | | |
|---|---|---|---|
| 2,542,542 | 2/1951 | Lippincott et al. | 252/56 |
| 2,683,736 | 7/1954 | Kosmin . | |
| 2,699,427 | 1/1955 | Smith et al. | 44/410 |
| 2,860,040 | 11/1958 | Fischl . | |
| 2,923,645 | 2/1960 | Miller . | |
| 3,048,479 | 8/1962 | Ilnyckyj et al. | 44/62 |
| 3,055,928 | 9/1962 | Flores . | |

(List continued on next page.)

FOREIGN PATENT DOCUMENTS

| | | |
|---|---|---|
| 0061895 | 10/1982 | European Pat. Off. . |
| 0153176 | 8/1985 | European Pat. Off. . |
| 0153177 | 8/1985 | European Pat. Off. . |
| 0261957 | 3/1988 | European Pat. Off. . |
| 0261958 | 3/1988 | European Pat. Off. . |
| 0261959 | 3/1988 | European Pat. Off. . |
| 1209676 | 10/1970 | United Kingdom . |
| 1263152 | 2/1972 | United Kingdom . |
| 1468588 | 3/1977 | United Kingdom . |
| 1469016 | 3/1977 | United Kingdom . |
| 2129012 | 5/1984 | United Kingdom . |

OTHER PUBLICATIONS

Aldrich Chemical Co, Inc., Cmpd 33,042–6 "Nitrophthalamide," p. 394, WI., 1992.
Journal of the Institute of Petroleum vol. 52, No. 510, Jun. 1966, pp. 173–185.

Primary Examiner—Margaret Medley
Attorney, Agent, or Firm—John J. Mahon

[57]  ABSTRACT

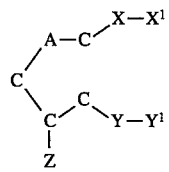

Compounds of general formula (I) wherein X and Y are the same or different and are selected from the group consisting of $SO_3(—)$, $—CO—$, $—C(O)O(—)$, $—R^4—C(O)O—$, $—NR^3C(O)—$, $—R^4O—$, $—R^4—C(O)O—$, $—R^4—$ and $—NC(O)—$, $R^4$ being $—(CH_2)_m—$ where m is from 0 to 5 and $R^3$ is defined below; $X^1$ and $Y^1$ are the same or different and are selected from the group consisting of (a), $R^1$ and $R^2$ being independently selected from the group consisting of alkyl, alkoxy alkyl or polyalkoxyalkyl groups that contain at least 10 carbon atoms in their main chain, and $R^3$ being a hydrocarbyl group, each $R^3$ in a compound of formula (I) being the same of different; A is, together with the carbon atoms with which it constitutes the ring structure in formula (I), an aromatic, non-aromatic, or aliphatic group, where any of such groups can be mono- or polycyclic and/or can include one or more hetero atoms selected from nitrogen, sulphur and oxygen; and Z is selected from nitro, hydroxy, alkyl, alkoxy, carboxy acid and carboxy ester, and their use as low temperature flow improvers for distillate fuels.

5 Claims, 7 Drawing Sheets

U.S. PATENT DOCUMENTS

| | | | |
|---|---|---|---|
| 3,095,286 | 6/1963 | Andress, Jr. et al. | 44/408 |
| 3,252,771 | 5/1966 | Clough et al. | 44/62 |
| 3,444,082 | 5/1969 | Kautsky | 252/51.5 |
| 3,481,939 | 12/1969 | Brannock . | |
| 3,691,123 | 9/1972 | Clarke et al. . | |
| 3,892,768 | 7/1975 | Alvino et al. . | |
| 3,961,916 | 6/1976 | Ilnyckyj et al. | 44/62 |
| 4,055,358 | 10/1977 | Garner et al. . | |
| 4,113,463 | 9/1978 | Oshio . | |
| 4,211,534 | 7/1980 | Feldman . | |
| 4,375,973 | 3/1983 | Rossi et al. | 44/62 |
| 4,402,708 | 9/1983 | Oswald | 44/66 |
| 4,491,455 | 1/1985 | Ishizaki et al. | 44/62 |
| 4,810,262 | 3/1989 | Lewtas et al. | 44/408 |
| 4,863,486 | 9/1989 | Tack et al. | 44/408 |
| 5,045,088 | 9/1991 | More et al. | 44/393 |
| 5,102,427 | 4/1992 | Feldman et al. | 44/408 |

CHEMICAL COMPOSITIONS AND THEIR USE AS FUEL ADDITIVES

The invention relates to new chemical compounds which are useful as wax crystal modifiers in fuels especially distillate fuels, the use of these compounds as distillate fuel additives particularly in combination with other additives, and to fuels and concentrates containing the additives optionally in combinations with other additives.

Mineral oils containing paraffin wax have the characteristic of becoming less fluid as the temperature of the oil decreases. This loss of fluidity is due to the crystallisation of the wax into plate-like crystals which eventually form a spongy mass entrapping the oil therein. The temperature at which the wax crystals begin to form is known as the Cloud Point and the temperature at which the wax prevents the oil from pouring as the Pour Point. Between these temperatures the wax crystals can however block filters rendering systems such as diesel trucks and domestic heating systems inoperable.

It has long been known that various additives act as wax crystal modifiers when blended with waxy mineral oils. These compositions modify the size and shape of wax crystals and reduce the cohesive forces between the crystals and between the wax and the oil in such a manner as to permit the oil to remain fluid at lower temperatures and in some instances to have improved filterability at temperatures between the cloud point and the pour point.

Various Pour Point depressants have been described in the literature and several of these are in commercial use. For example, U.S. Pat. No. 3,048,479 describes the use of copolymers of ethylene and $C_1$–$C_5$ vinyl esters, e.g. vinyl acetate, as pour depressants for fuels, specifically heating oils, diesel and jet fuels. Hydrocarbon polymeric pour depressants based on ethylene and higher alpha-olefins, e.g. propylene, are also known.

U.S. Pat. No. 3,961,916 describes the use of a mixture of copolymers, to control the size of the wax crystals and United Kingdom Patent 1,263,152 states that the size of the wax crystals may be controlled by using a copolymer having a low degree of side chain branching. Both systems improve the ability of the fuel to pass through filters as determined by the Cold Filter Plugging Point (CFPP) test because, instead of the plate like crystals that are formed without the presence of additives, the wax crystals produced are needle shaped and will not block the pores of the filter rather forming a porous cake on the filter allowing passage of the remaining fluid.

Other additives have also been proposed. For example, United Kingdom Patent 1,469,016 states that the copolymers of di-n-alkyl fumarate and vinyl acetate which have previously been used as pour depressants for lubricating oils may be used as co-additives with ethylene/vinyl acetate copolymers in the treatment of distillate fuels with high final boiling points to improve their low temperature flow properties.

U.S. Pat. No. 3,252,771 describes the use of polymers of $C_{16}$ to $C_{18}$ alpha-olefins obtained by polymerising olefin mixtures that predominate in normal $C_{16}$ to $C_{18}$ alpha-olefins with aluminium trichloride/alkyl halide catalysts as pour depressants in distillate fuels of the broad boiling, easy-to-treat types available in the United States in the early 1960's.

It has also been proposed to use additives based on olefin/maleic anhydride copolymers. For example, U.S. Pat. No. 2,542,542 describes copolymers of olefins such as octadecene with maleic anhydride esterified with an alcohol such as lauryl alcohol as pour depressants and United Kingdom Patent 1,468,588 describes copolymers of $C_{22}$–$C_{28}$ olefins with maleic anhydride esterified with behenyl alcohol as coadditives for distillate fuels.

Similarly, Japanese Patent Publication 5,654,037 describes olefin/maleic anhydride copolymers which have been reacted with amines as pour point depressants and Japanese Patent Publication 5,654,038 describes using derivatives of olefin/maleic anhydride copolymers together with conventional middle distillate flow improvers such as ethylene vinyl acetate copolymers.

Japanese Patent Publication 5,540,640 describes the use of olefin/maleic anhydride copolymers (not esterified) and states that the olefins used should contain more than 20 carbon atoms to obtain CFPP activity.

United Kingdom Patent 2,129,012 describes using mixtures of esterified olefin/maleic anhydride copolymers and low molecular weight polyethylene, the esterified copolymers being ineffective when used as sole additives. The patent specifies that the olefin should contain 10–30 carbon atoms and the alcohol 6–28 carbon atoms with the longest chain in the alcohol containing 22–40 carbon atoms.

U.S. Pat. Nos. 3,444,082; 4,211,534; 4,375,973 and 4,402,708 describe the use of certain nitrogen containing compounds.

Long n-alkyl derivatives of difunctional compounds have also been described as has their use as wax crystal modifiers for distillate fuels, i.e. derivatives, particularly amine derivatives of alkenyl succinic acid (U.S. Pat. No. 3,444,082), maleic acid (U.S. Pat. No. 4,211,534) and phthalic acid (GB 2923645, U.S. Pat. No. 4,375,973 and U.S. Pat. No. 4,402,708). Amine salts of certain alkylated aromatic sulphonic acids are described in United Kingdom Patent Specification 1209676 as is their use as antirust additives for turbine oils and hydraulic oils.

The improvement in CFPP activity achieved by the incorporation of the additives described in the above-mentioned patent specification is achieved by modifying the size and shape of the wax crystals forming to produce needle like crystals generally of particle size 10,000 nanometres or bigger typically 30,000 to 100,000 nanometres. In operation of diesel engines or heating systems at low temperatures, these crystals do not generally pass through the filters but form a permeable cake on the filter allowing the liquid fuel to pass. The wax crystals will subsequently dissolve as the engine and the fuel heats up, which can be by the bulk fuel being heated by recycled fuel. This can, however, result in the wax crystals blocking the filters, leading to starting problems and problems at the start of driving in cold weather or failure of fuel heating systems.

European Patent Publications 0261957, 0261958, 0261959 describe the use as additives of compounds having a certain configuration and in particular certain novel compounds which make possible a significant reduction in the size of the wax crystals formed to below 4,000 nanometres sometimes below 2,000 nanometres and in some instances below 1,000 nanometres.

Further compounds have now been devised whose performance in controlling the size of wax crystals in distillate fuels is comparable to that of the compounds described in EP-A-0261959.

This invention therefore provides in one aspect a compound of the general formula

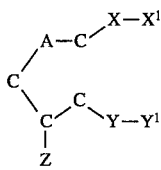 (I)

wherein X and Y are the same or different and are selected from the group consisting of $SO_3^{(-)}$, —CO—, —C(O)O$^{(-)}$, —$R^4$—C(O)O—, —$NR^3$C(O)—, —$R^4$O—, —$R^4$OC(O)—, —$R^4$— and —NC(O)—, $R^4$ being —$(CH_2)_m$— where m is from 0 to 5 and $R^3$ is defined as below;

$X^1$ and $Y^1$ are the same or different and are selected from the group consisting of
$N^{(+)}R_3^3R^2$, $HN^{(+)}R_3^3R^2$, $H_2N^{(+)}R^3R^2$, $H_3N^{(+)}R^2$, $N^{(+)}R^3R^1$, $N^{(+)}HR_3^3R^1$, $H_2N^{(+)}R^3R^1$, $H_3N^{(+)}R^1$, $NR^3R^2$, —$R^2$, —$NR^3R^1$ and $R^1$, $R^1$ and $R^2$ being independently selected from the group consisting of alkyl, typically $C_{10}$ to $C_{40}$ more preferably $C_{10}$ to $C_{30}$ more preferably $C_{14}$ to $C_{24}$, alkoxy alkyl or polyalkoxyalkyl groups that contain at least 10, typically 10 to 40, carbon atoms in their main chain, and $R^3$ being a hydrocarbyl group, preferably alkyl, more preferably $C_1$ to $C_{30}$ most preferably $C_{10}$ to $C_{30}$ straight chain, each $R^3$ in a compound of formula (I) being the same or different;

A is, together with the carbon atoms with which it constitutes the ring stucture in formula (I), an aromatic, non-aromatic, or aliphatic group, where any of such grounds can be mono- or poly-cyclic and/or can include one or more hetero atoms selected from nitrogen, sulphur and oxygen; and Z is selected from nitro, hydroxy, alkyl, alkoxy, carboxy acid and carboxy ester, any alkyl groups preferably containing from 1 to 10, more preferably 1 to 4, carbon atoms.

It is preferred that $X^1$ and $Y^1$ together contain at least three alkyl, alkoxy alkyl or polyalkoxy alkyl groups.

In a second aspect of the invention, a distillate fuel composition comprises a distillate petroleum fuel boiling in the range of 120° C. to 500° C. containing from 0.0001 to 0.5 wt % of a compound of formula (I).

In a third aspect of the invention, a compound of formula (I) is used as an additive for improving the low temperature flow properties of a distillate petroleum fuel.

In a fourth aspect of the invention, a concentrate comprises a compound of formula (I) in admixture with a solvent therefore, the solvent being compatible with a distillate petroleum fuel.

The cyclic part of the structure of the compound of the present invention may be mono-cyclic or polycyclic aromatic or aliphatic, polynuclear aromatic, heteroaromatic, and heteroalicyclic. The ring structure may be saturated or unsaturated with one or more unsaturations; with at least one ring containing 4 or more atoms, and it may be multicyclic, bridged and may be substituted.

Examples of suitable monocyclic ring structures are benzene, cyclohexane, cyclohexene, cyclopentane, pyridine and furan. The ring structure may contain additional substituents. Suitable polycyclic compounds, that is those having two or more ring structures, can take various forms. They can be (a) fused aromatic structures, (b) fused partially hydrogenated aromatic ring structures where at least one but not all rings are aromatic, (c) alicyclic which includes fused alicyclic, bridged alicyclic, spiro alicyclic compounds (d) hydrocarbon ring assemblies of like or unlike rings which may be aromatic, alicyclic or mixed; (e) any of (a) to (d) which contain at least one hetero atom.

Fused aromatic structures from which the compounds may be derived include for example naphthalene, anthracene, phenathrene, fluorene, pyrene and indene. Suitable condensed ring structures where none or not all rings are benzene include for example azulene, hydronaphthalene, hydroindene, hydrofluorene, diphenylene. Suitable bridged alicyclic structures include bicycloheptane and bicycloheptene.

Suitable ring assemblies include biphenyl and cyclohexyl benzene.

Suitable heteropolycyclic structures include quinuclidine and indole.

Suitable heterocyclic compounds from which the compounds of this invention may be derived include quinoline; indole, 2,3 dihydroindole, benzofuran, coumarin and isocoumarin, benzothiophene, carbazole and thiodiphenylamine.

Suitable non-aromatic or partially saturated ring systems include decalin (decahydronaphthalene), d-pinene, cadinene, bornylene. Suitable bridged compounds include norbornene, bicycloheptane (norbornane), bicyclo octane and bicyclo octene.

When the cyclic structure is polycyclic, X and Y are preferably attached to adjoining ring atoms located completely within a single ring. For example if the structure were naphthalene, these substituents would preferably be attached to the 1,2-, 2,3-, 3,4-, 5,6-, 6,7- or 7,8- positions rather than to the 1,8- or 4,5- positions.

It has surprisingly been found that the presence of the group Z in the position shown in the cyclic structure in formula (I) leads to a significant improvement in the ability of the product, when used as an additive in distillate fuels, to control the size of the wax crystals that form in the fuel as it cools. The group Z is preferably a nitro group for use of compounds of formula (I) as distillate additives. For good performance as a fuel additive it is preferred that Z be in the 3- position on the ring relative to a cationic nitrogen in $X^1$ and/or $Y^1$ when one is present. Thus for example a compound of the formula (II)

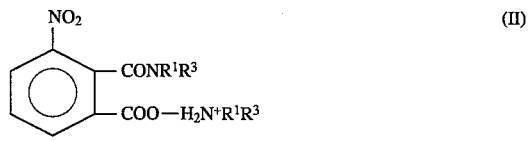 (II)

has considerably greater activity than a compound of the formula (III)

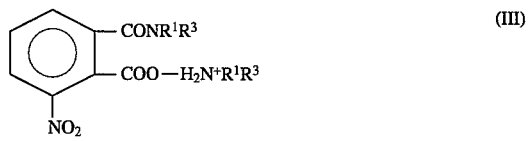 (III)

A possible factor in the performance of the additive is believed to be due to its solubility in the fuel which can depend upon the substituent groups.

The preferred compounds of the present invention are of the formula (VI):

 (VI)

more preferably of the formula (VII)

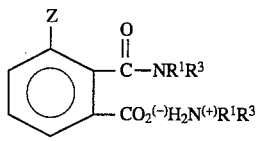

$R^1$ and $R^3$ being each preferably $C_{16/18}$ alkyl or $C_{17/18}$ alkyl.

It has been found that by using the novel compounds of the present invention as additives for distillate fuels the wax crystals which form as the fuel cools can be sufficiently small to pass through the filters of typical diesel engines and heating systems rather than forming a cake on the filter.

It has also been found that this reduction of wax crystal size according to the invention reduces the tendency of the wax crystals to settle in the fuel during storage and can also result in a further improvement in the CFPP performance of the fuel.

The Wax Appearance Temperature (WAT) of the fuel is measured by differential scanning calorimetry (DSC). In this test a small sample of fuel (25㎣) is cooled at 2° C./minute together with a reference sample of similar thermal capacity but which will not precipitate wax in the temperature range of interest (such as kerosene). An exotherm is observed when crystallisation commences in the sample. For example the WAT of the fuel may be measured by the extrapolation technique on the Mettler TA 2000B.

The wax content is derived from the DSC trace by integrating the area enclosed by the baseline and the exotherm down to the specified temperature, the calibration having been previously performed on a known amount of crystallizing wax.

The wax crystal average particle size is measured by analysing a Scanning Electron Micrograph of a fuel sample at a magnification of 4000 to 8000× and measuring the longest axis of 50 crystals over a predetermined grid. We find that providing the average size is less than 4000 nanometres the wax will begin to pass through the typical paper filters used in diesel engines together with the fuel although we prefer that the size be below 3000 nanometres, more preferably below 2000 and most preferably below 1000 nanometres, the actual size attainable depends upon the original nature of the fuel and the nature and amount of additive used but we have found that these sizes and smaller are attainable.

Fuels containing compounds of formula (I) as additives have outstanding benefits when compared with distillate fuels whose cold flow properties have been improved by the addition of conventional additives. For example the fuels are operable at temperatures approaching the pour point and not restricted by the inability to pass the CFPP test. Hence these fuels either pass the CFPP test at significantly lower temperatures or obviate the need to pass that test. The fuels also have improved coldstart performance at low temperatures since they do not rely on recirculation of warm fuel to dissolve undesirable wax deposits. The fuels also have a reduced tendency for the wax crystals to settle in the fuel during storage reducing the tendency for wax to agglomerate at the bottom of storage vessels so blocking filters, etc.

Small crystals may be obtained by adding the compounds of the invention to a distillate fuel oil, the amount of the compound added being preferably 0.0001 to 0.5 wt. %, for example 0.01 to 0.10 wt. %, based on the weight of fuel.

The compounds of the invention may conveniently be dissolved in a suitable solvent to form a concentrate of from 20 to 90, e.g. 30 to 80 weight % in the solvent. Suitable solvents include kerosene, aromatic naphthas, mineral lubricating oils etc.

When the compounds are used as distillate fuel additives it is preferred that $R^1$, $R^2$, and $R^3$ when present contain 10 to 24 carbon atoms, for example 14 to 22 preferably 18 to 22 carbon atoms and are preferably straight chain or branched at the 1 or 2 position. Suitable alkyl groups include decyl, dodecyl, tetradecyl, hexadecyl, octadecyl, eicosyl and docosyl (behenyl). Alternatively the groups may be polyethylene oxide or polypropylene oxide, the main chain of the groups being the longest linear segment.

The especially preferred compounds defined by formula (I) are the amides or amine salts of secondary amines.

Although three substituents are necessary, as shown in the formulae, it should be realised that the compounds can contain one or more further substituents attached to ring atoms of the cyclic compounds.

The compounds of the present invention are preferably prepared from a reactant such as that of formula (IV):

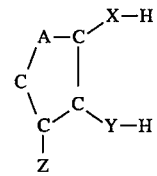

where X and Y are as defined in respect of formula (I) and additionally can together form part of a cyclic anhydride structure wherein an oxy group (>O) is common to both X and Y.

Preferred reactants of formula (IV) are those in which X and Y are selected from —C(O)O— and —SO$_3^{(-)}$ and particularly preferred reactants are compounds of the formula (V):

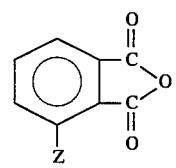

The compounds of the present invention are prepared by reacting both the Y-H group and the X-H group of formula (IV) with, for example, amines, alcohols, quaternary ammonium salts or mixtures thereof. It has been found that the presence of the Z group next to an anhydride ring (as in formula (V)) encourages formation of an amide group on the carbon atom adjacent to the carbon atom carrying Z thus yielding a product which is predominantly the preferred compound although some amounts of the less preferred compound, i.e. where the amide group is further from Z, may also be obtained. Where the final compounds are the amides or amine salts they are preferably of a secondary amine which has a hydrogen and carbon containing group containing at least 10 carbon atoms preferably a straight chain alkyl group containing from 10 to 30 more preferably 16 to 24 carbon atoms. Such amides or salts may be prepared by reacting the acid or anhydride with a secondary amine or alternatively by reaction with an amine derivative. Removal of water and heating are generally necessary to prepare the amides from the acids. Alternatively the Y-H and X-H groups may be reacted with an alcohol containing at least 10 carbon atoms or a mixture of an alcohol and an amine or sequentially with an amine and an alcohol or vice-versa.

Thus, the final compounds comprise, depending on the identity of X-X$^1$, and Y-Y$^1$ for example esters, amides, ethers, primary, secondary or tertiary amine salts, amino amides and amino ethers.

Although the compounds of the invention are useful as sole additives, the best effect is usually obtained when they are used in combination with other additives known for improving the cold flow properties of distillate fuels.

The compounds are preferably used together with what are known as comb polymers of the general formula

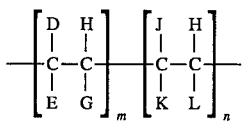

where

D=R, C(O).OR, OC(O).R, R'C(O).OR or OR
E=H or CH$_3$ or D or R'
G=H, or D
m=1.0 (homopolymer) to 0.4 (mole ratio)
J=R' Aryl or Heterocyclic group, R'CO.OR
K=H, C(O).OR', OC(O).R', OR', C(O)OH
L=H, R', C(O).OR', OC(O).R', Aryl, C(O)OH
n=0.0 to 0.6 (mole ratio)
R is a hydrocarbyl group containing more than 10 carbon atoms, preferably from 10 to 30 carbon atoms
R' is a C$_1$ to C$_{30}$ hydrocarbyl group.

Another monomer may be terpolymerized if necessary.

Examples of suitable comb polymers are the fumarate/vinyl acetate particularly those described in our European Patent Publications 0153176 and 0153177 and esterified olefine/maleic anhydride copolymers and the polymers and copolymers of alpha olefines and esterified copolymers of styrene and maleic anhydride.

Examples of other additives with which the compounds of the present invention may be used are the polyoxyalkylene esters, ethers, ester/ethers and mixtures thereof, particularly those containing at least one, preferably at least two C$_{10}$ to C$_{30}$ linear saturated alkyl groups and a polyoxyalkylene glycol group of molecular weight 100 to 5,000 preferably 200 to 5,000, the alkyl group in said polyoxyalkylene glycol containing from 1 to 4 carbon atoms. These materials form the subject of European Patent Publication 0,061,895 A2. Other such additives are described in U.S. Pat. No. 4,491,455.

The preferred esters, ethers or ester/ethers which may be used may be structurally depicted by the formula:

R—O(A)—O—R"

where R and R" are the same or different and may be

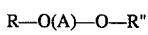 i)

 ii)

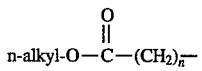 iii)

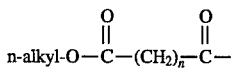 iv)

the alkyl group being linear and saturated and containing 10 to 30 carbon atoms, and A represents the polyoxyalkylene segment of the glycol in which the alkylene group has 1 to 4 carbon atoms, such as polyoxymethylene, polyoxyethylene or polyoxytrimethylene moiety which is substantially linear; some degree of branching with lower alkyl side chains (such as in polyoxypropylene glycol) may be tolerated but it is preferred the glycol should be substantially linear, A may also contain nitrogen.

Suitable glycols generally are the substantially linear polyethylene glycols (PEG) and polypropylene glycols (PPG) having a molecular weight of about 100 to 5,000, preferably about 200 to 2,000. Esters are preferred and fatty acids containing from 10–30 carbon atoms are useful for reacting with the glycols to form the ester additives and it is preferred to use a C$_{18}$–C$_{24}$ fatty acid, especially behenic acids. The esters may also be prepared by esterifying polyethoxylated fatty acids or polyethoxylated alcohols.

Polyoxyalkylene diesters, diethers, ether/esters and mixtures thereof are suitable as additives with diesters preferred for use in narrow boiling distillates whilst minor amounts of monoethers and monoesters may also be present and are often formed in the manufacturing process. It is important for additive performance that a major amount of the dialkyl compound is present. In particular, stearic or behenic diesters of polyethylene glycol, polypropylene glycol or polyethylene/polypropylene glycol mixtures are preferred.

The compounds of this invention may also be used with ethylene unsaturated ester copolymer flow improvers. The unsaturated monomers which may be copolymerised with ethylene include unsaturated mono and diesters of the general formula:

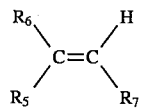

wherein R$_6$ is hydrogen or methyl, R$_5$ is a —OOCR$_8$ group wherein R$_8$ is hydrogen formate or a C$_1$ to C$_{28}$, more usually C$_1$ to C$_{17}$, and preferably a C$_1$ to C$_8$, straight or branched chain alkyl group; or R$_5$ is a —COOR$_8$ group wherein R$_8$ is as previously described but is not hydrogen and R$_7$ is hydrogen or —COOR$_8$ as previously defined.

The monomer, when R6 and R$_7$ are hydrogen and R5 is —OOCR$_8$, includes vinyl alcohol esters of C$_1$ to C$_{29}$, more usually C$_1$ to C5, monocarboxylic acid, and preferably C$_2$ to C$_{29}$, more usually C$_1$ to C5 monocarboxylic acid, and preferably C$_2$ to C$_5$ monocarboxylic acid. Examples of vinyl esters which may be copolymerised with ethylene include vinyl acetate, vinyl propionate and vinyl butyrate or isobutyrate, vinyl acetate being preferred. We prefer that the copolymers contain from 5 to 40 wt. % of the vinyl ester, more preferably from 10 to 35 wt. % vinyl ester. They may also be mixtures of two copolymers such as those described in U.S. Pat. No. 3,961,916. It is preferred that these copolymers have a number average molecular weight as measured by vapour phase osmometry of 1,000 to 10,000, preferably 1,000 to 5,000.

The compounds of the invention may also be used in distillate fuels in combination with other polar compounds, either ionic or non-ionic, which have the capability in fuels of acting as wax crystal growth inhibitors. We have surprisingly found that the use of the compounds of the present invention together with these other polar nitrogen compounds can have a synergistic effect. Polar nitrogen containing compounds have been found to be especially effective when used in combination with the glycol esters, ethers or ester/ethers and such three component mixtures are within the scope of the present invention. These polar compounds are generally amine salts and/or amides formed by reaction of at least one molar proportion of hydrocarbyl substituted amines with a molar proportion of hydrocarbyl acid having 1 to 4 carboxylic acid groups or their anhydrides; ester/amides may also be used containing 30 to 300, preferably 50 to 150 total carbon atoms. These nitrogen compounds are described in U.S. Pat. No. 4,211,534. Suitable amines are usually long chain $C_{12}-C_{40}$ primary, secondary, tertiary or quaternary amines or mixtures thereof but shorter chain amines may be used provided the resulting nitrogen compound is oil soluble and therefore normally containing about 30 to 300 total carbon atoms. The nitrogen compound preferably contains at least one straight chain $C_8$ to C40, preferably $C_{14}$ to $C_{24}$ alkyl segment.

Suitable amines include primary, secondary, tertiary or quaternary, but preferably are secondary. Tertiary and quaternary amines can only form amine salts. Examples of amines include tetradecyl amine, cocoamine, hydrogenated tallow amine and the like. Examples of secondary amines include dioctacedyl amine, methyl-behenyl amine and the like. Amine mixtures are also suitable and many amines derived from natural materials are mixtures. The preferred amine is a secondary hydrogenated tallow amine of the formula $HNR_1R_2$ where in $R_1$ and $R_2$ are alkyl groups derived from hydrogenated tallow fat composed of approximately 4% $C_{14}$, 31% $C_{16}$, 59% $C_{18}$.

Examples of suitable carboxylic acids and their anhydrides for preparing these nitrogen compounds include cyclohexane, 1,2 dicarboxylic acid, cyclohexene, 1,2- dicarboxylic acid, cyclopentane 1,2 dicarboxylic acid, naphthalene dicarboxylic acid and the like. Generally, these acids will have about 5–13 carbon atoms in the cyclic moiety. Preferred acids useful in the present invention are benzene dicarboxylic acids such as phthalic acid, isophthalic acid, and terephthalic acid. Phthalic acid or its anhydride is particularly preferred. The particularly preferred compound is the amide-amine salt formed by reacting 1 molar portion of phthalic anhydride with 2 molar portions of di-hydrogenated tallow amine. Another preferred compound is the diamide formed by dehydrating this amide-amine salt.

Hydrocarbon polymers may also be used as part of the additive combination which may be represented with the following general formula:

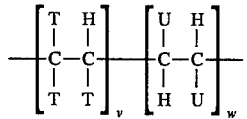

where
T=H or $R^1$
U=H, T or Aryl
v=1.0 to 0.0 (mole ratio)
w=0.0 to 1.0 (mole ratio)
where $R^1$ is alkyl.

These polymers may be made directly from ethylenically unsaturated monomers or indirectly by hydrogenating the polymer made from monomers such as isoprene, butadiene etc.

A particularly preferred hydrocarbon polymer is a copolymer of ethylene and propylene having an ethylene content preferably between 20 and 60% (w/w) and is commonly made via homogeneous catalysis.

The compounds may also be used together with compounds similar to those described in our European Patent Application 0261959 as having the general formula

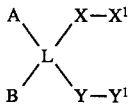

where
A and B may be the same or different and may be alkyl, alkenyl or aryl;

L is selected from the group consisting of

>CH—CH< and >C=C< and A, B and L together can constitute part of a cyclic structure which can be aromatic, alicyclic or mixed aromatic/alicyclic, and with the proviso that the groups —X—$X^1$ and Y—$Y^1$ are located on different carbon atoms constituting L and in that when A, B and L do not constitute part of a cyclic structure one of A or B may be hydrogen and in that when L is non-cyclic ethylenic, said X—$X^1$ and Y—$Y^1$ groupings are present in a cis configuration;

X is selected from the group consisting of
$SO_3^{(-)}$, —C(O)—, —C(O)O$^{(-)}$, —$R^4$—C(O)O—, —$NR^3$C(O)— —$R^4$O—, —$R^4$OC(O)—, —$R^4$— and —NC(O)—;

$X^1$ is selected from the group consisting of
$N^{(+)}R_3^3R^2$, $HN^{(+)}R_2^3R^2$, $H_2N^{(+)}R^3R^2$, $H_3N^{(+)}R^2$, $N^{(+)}R_3^3R^1$, $N^+HR_2^3R^1$, $H_2N^{(+)}R_3^3R^1$, $H_3N^{(+)}R^1$, $NR^3R^2$, —$R^2$, —$NR^3R^1$, and $R^1$;

Y is —$SO_3^{(-)}$ or —$SO_2$;

when Y is $SO_3^{(-)}$ $Y^1$ is selected from the group consisting of $N^{(+)}R_3^3R^2$, $HN^{(+)}R_2^3R^2$, $H_2N^{(+)}R^3R^2$ and $H_3N^{(+)}R^2$ and when Y is —$SO_2$—$Y^1$ is —$OR^2$, —$NR^3R^2$ or —$R^2$ and wherein $R^1$ and $R^2$ are independently selected from the group consisting of alkyl, alkoxy alkyl or polyalkoxyalkyl groups containing at least 10 carbon atoms in their main chain;

$R^3$ is hydrocarbyl and each $R^3$ may be the same or different; and $R^4$ is —$(CH_2)_n$— where n is from 0 to 5.

The invention is illustrated by the following Examples in which reference will be made to the accompanying figures wherein FIG. 1 is an IR trace of Additive A;

The following additives were prepared as described.

Additives coded A and H are compounds of the invention.

Figure 1:
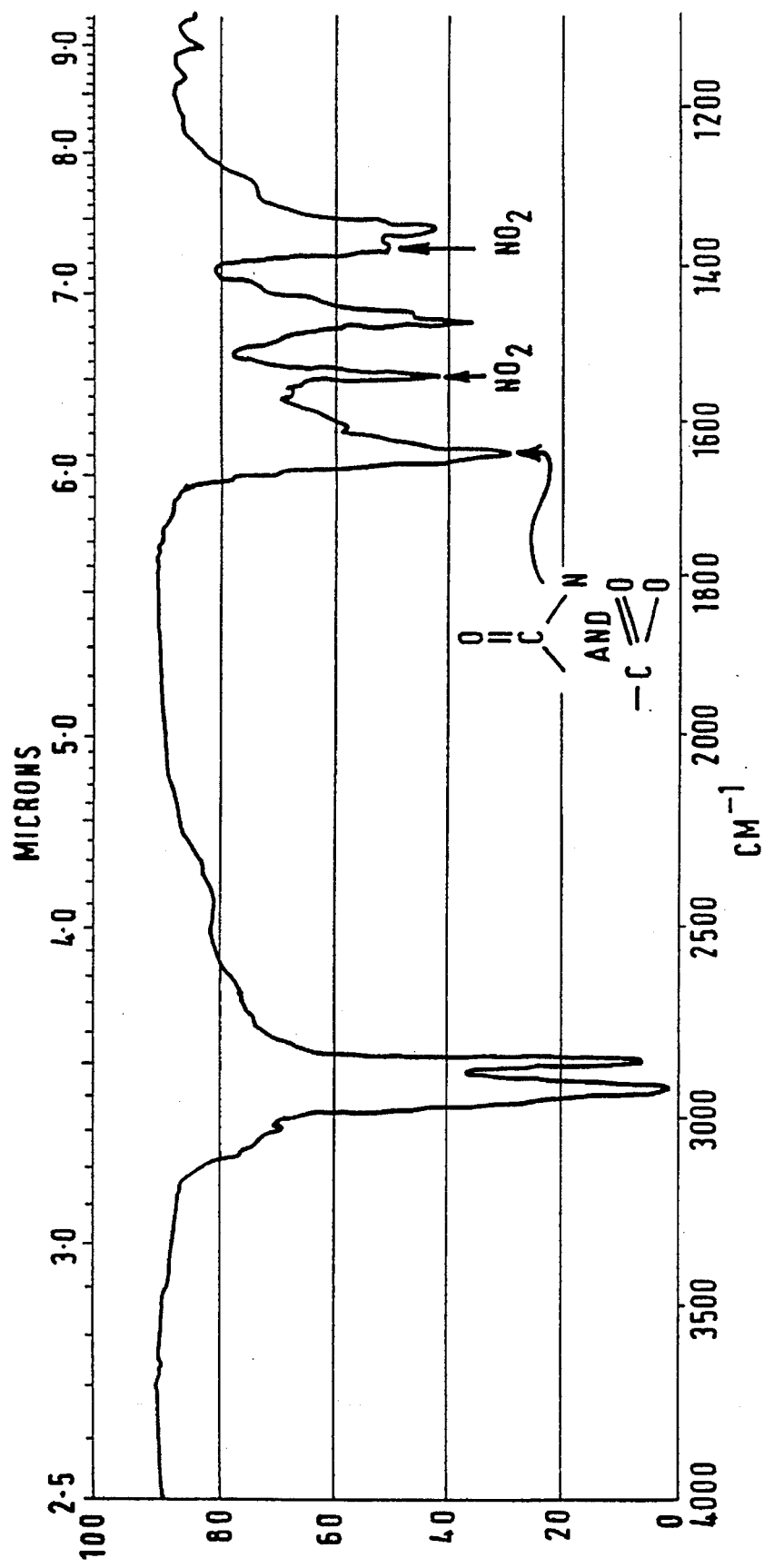
Figure 2:
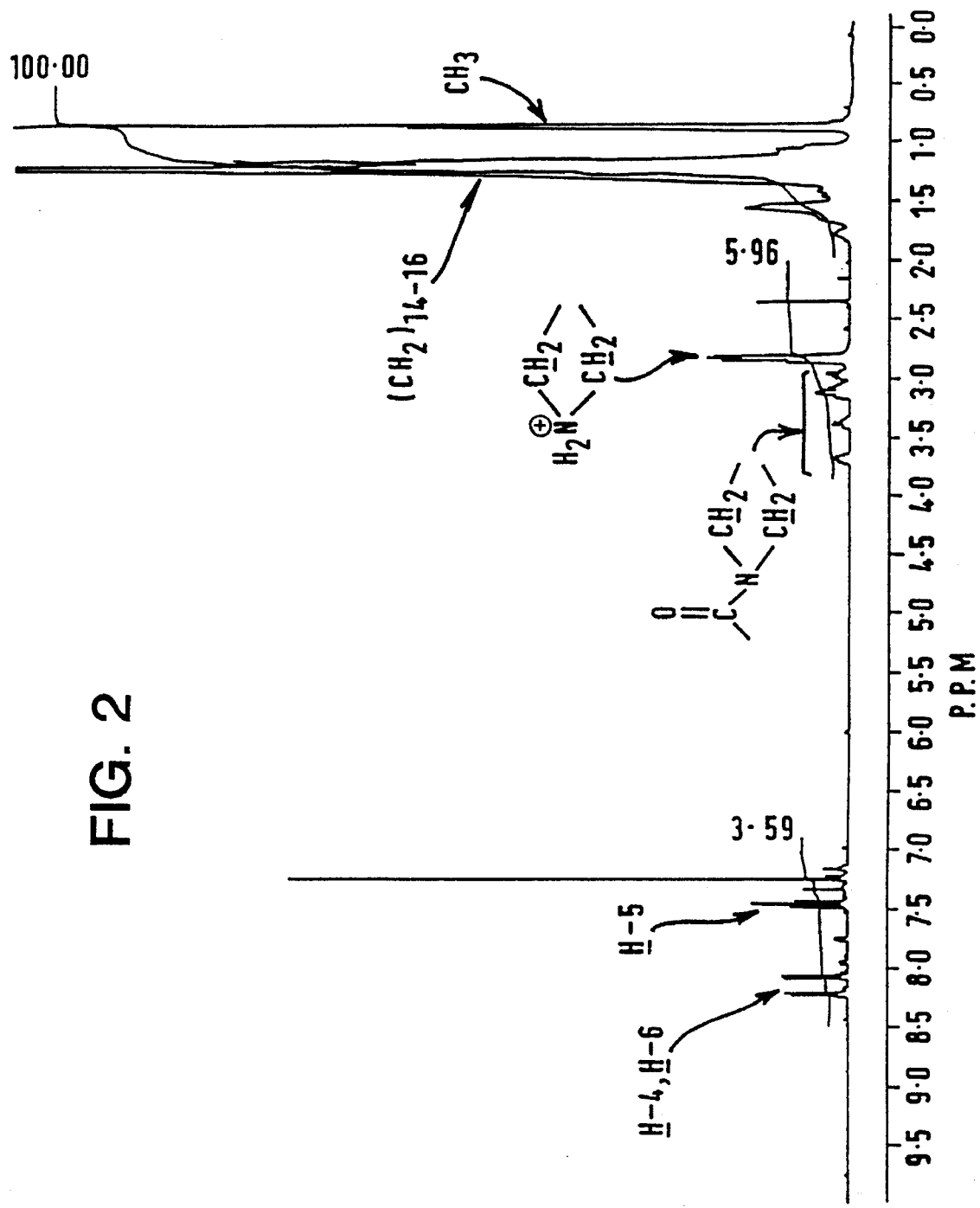
FIG. 2 is a proton NMR trace of Additive A.

Additive A 3-nitro phthalic anhydride (commercially available) was reacted with two moles of dihydrogenated tallow amine in a toluene solvent at 50% (w/w) concentration. The reaction mixture was stirred at 60° C. for 15 mins and the solvent removed by evaporation under reduced pressure at 50° C. to form a half amide/half amino salt whose structure, represented by formula (IX) below:

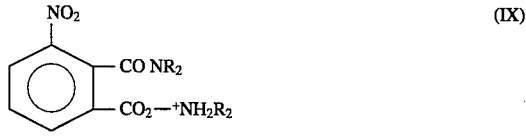

where R is $C_{16/18}$ alkyl, was confirmed by Infra red and proton NMR spectroscopy, the traces being FIGS. 1 and 2 hereof.

This product was coded Additive A when tested in distillate fuels and was tested together with certain of the following other additives in indicated hereinafter.

Additive B

A 1:1 molar styrene-maleic anhydride copolymer was esterified with 2 moles of $C_{14}H_{29}OH$ per mole of anhydride groups, the alcohol being used in a slight excess of approximately 5% alcohol. The esterification was catalysed by p-toluene sulphonic acid (1/10 mole) in xylene solvent. The product (coded additive B) had a number average molecular weight (Mn) of 50,000 and contained 3% (w/w) untreated alcohol.

Additive C

Additive C was made in a similar way to Additive B but using 2 moles of a 1:1 molar mixture of $C_{12}H_{25}OH$ and $C_{14}H_{29}OH$ to esterify the styrene maleic anhydride copolymer. This too gave a copolymer of number average molecular weight of 50,000 and contained 3.3% (w/w) free alcohol.

Additive D

An ethylene vinyl acetate copolymer having a number average molecular weight of 3,500 a vinyl acetate content of 13% and a side chain branching of 8 methyls/100 methylenes.

Additive E

The reaction product of phthalic anhydride and two moles of dihydrogenated tallow amine to form a half amide/half amine salt.

Additive F

The reaction product of pyromellitic dianhydride and four moles of dihydrogenated tallow amine to form the di(half amide/half amine salt).

Additive G

One mole of ortho-sulphobenzoic acid cyclic anhydride was reacted with 2 moles of di-(hydrogenated) tallow amine in a xylene solvent at 50% (w/w) concentration. The reaction mixture was stirred at between 100° C. and the refluxing temperature. The solvent and chemicals were kept as dry as possible to prevent the anhydride from being hydrolysed.

The product, coded Additive G, was shown by 500 MHz Nuclear Magnetic Resonance Spectroscopy to be the N,N-dialkyl ammonium salt of 2-dialkylamido benzene sulphonate where the alkyl groups are $nC_{16-18}H_{33-37}$, i.e. to have the formula (X) below:

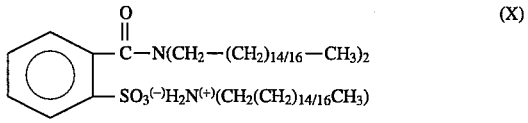

Additive H

Additive H, another compound of the invention, was prepared as follows:

3-carboxymethyl phthalic anhydride was treated with two moles of dihydrogenated tallow amine in a xylene solvent at 50% (w/w) concentration. The reaction mixture was stirred at 60° C. to form a half amide/half amino salt whose formula, (XI) below

Figure 3:
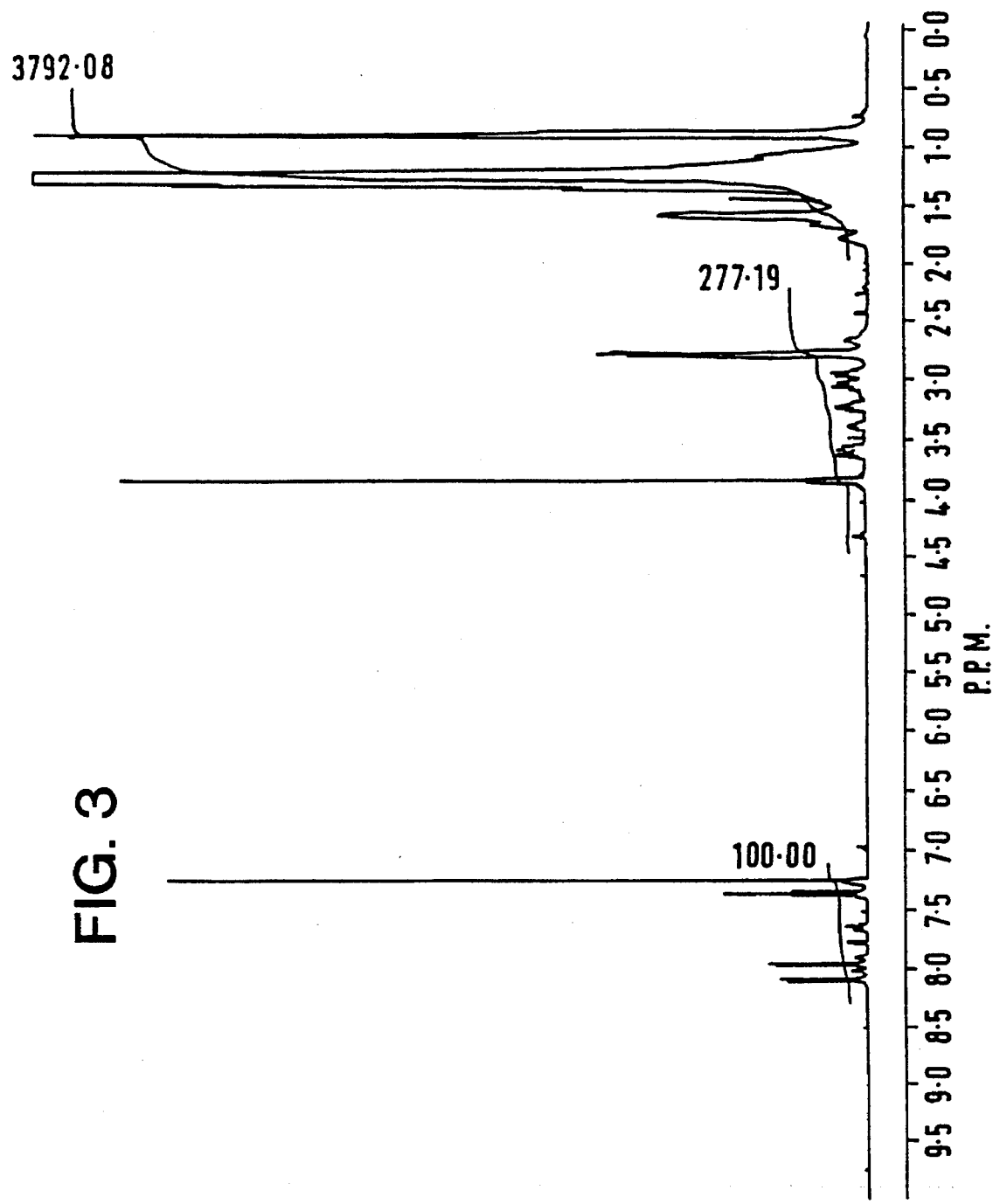
FIG. 3 is a proton NMR trace of Additive H.
Figure 4:
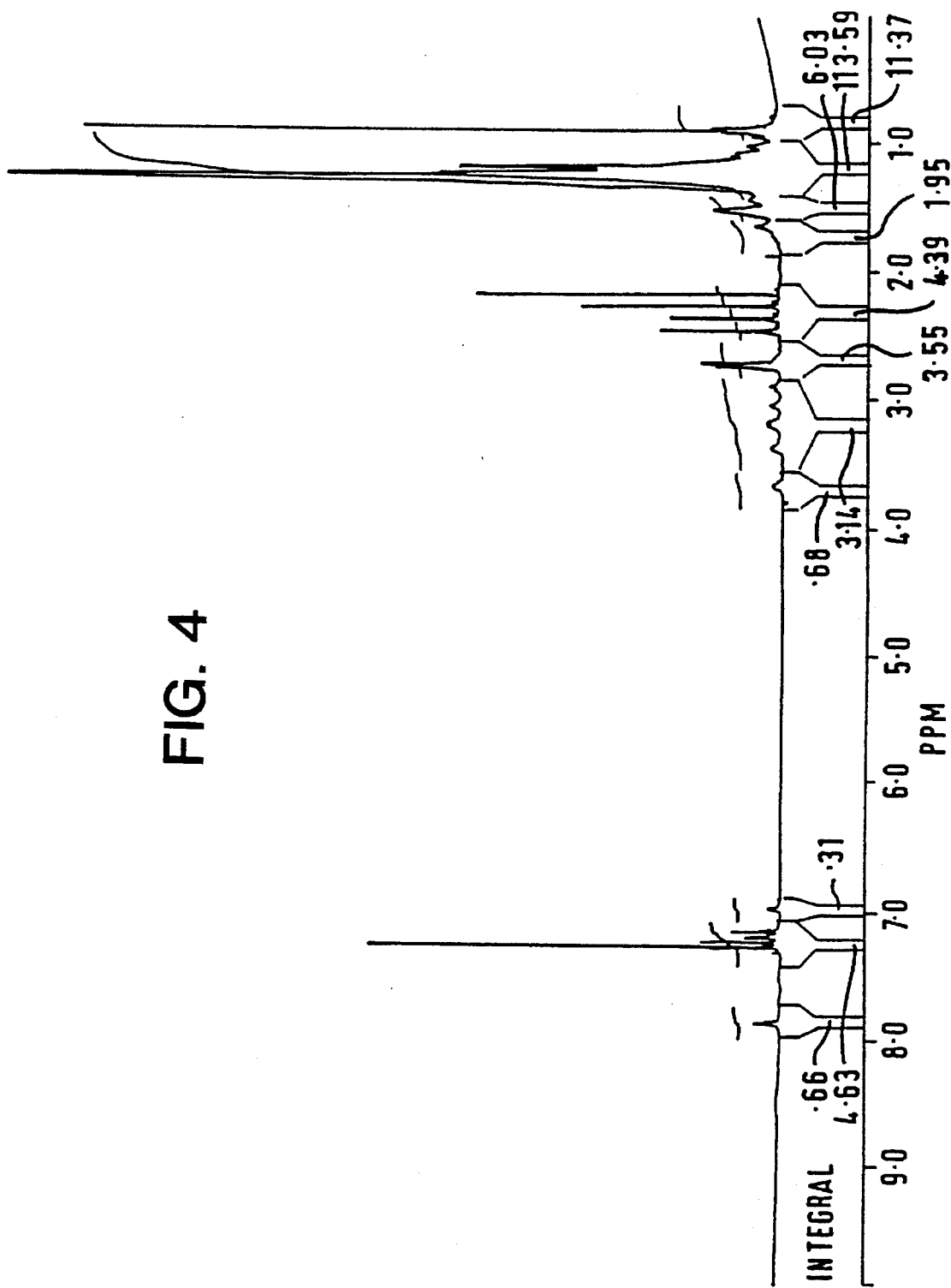
FIGS. 4–7 are each proton NMR traces of compounds of the present invention.
Figure 5:
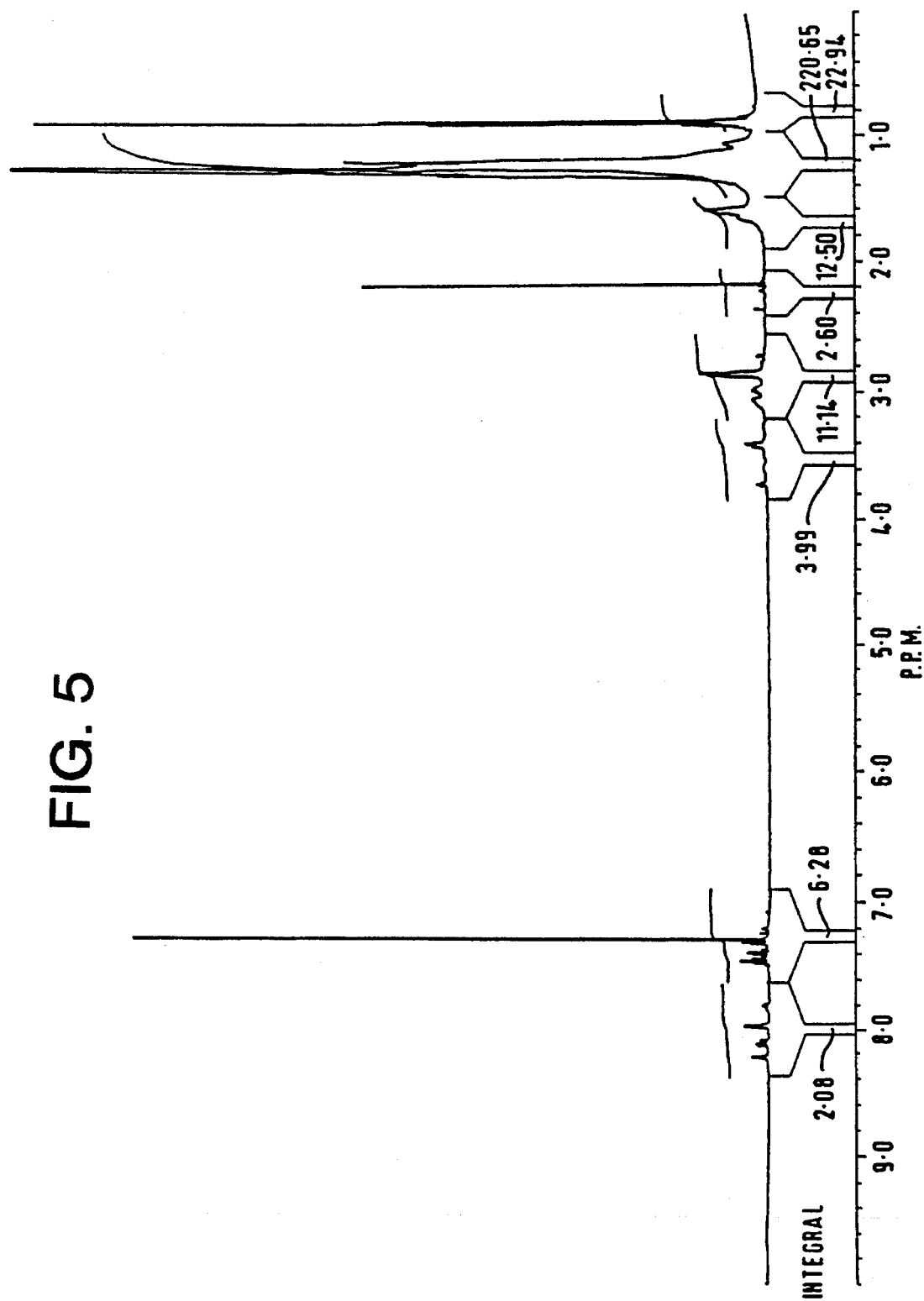
Figure 6:
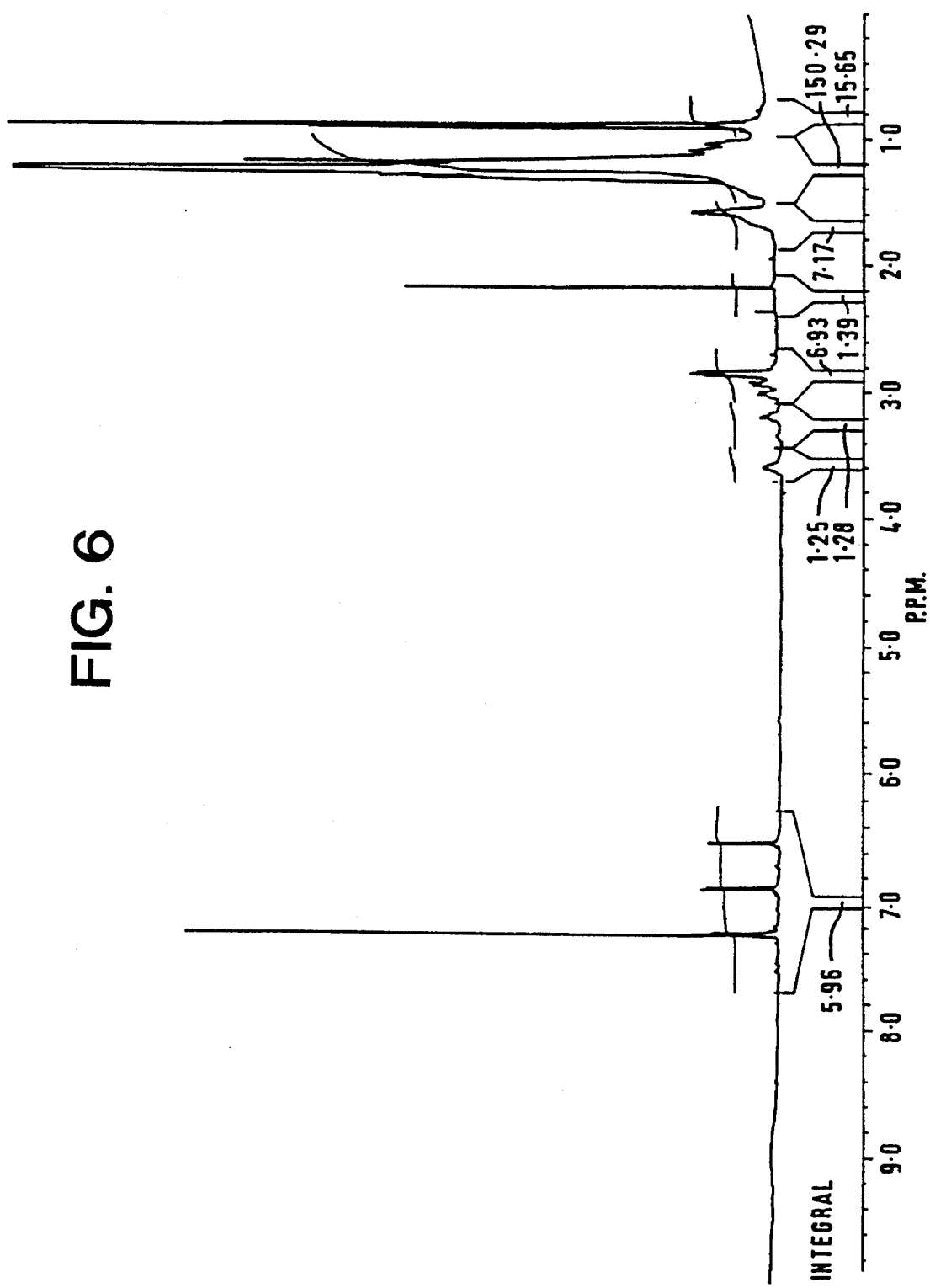
Figure 7:
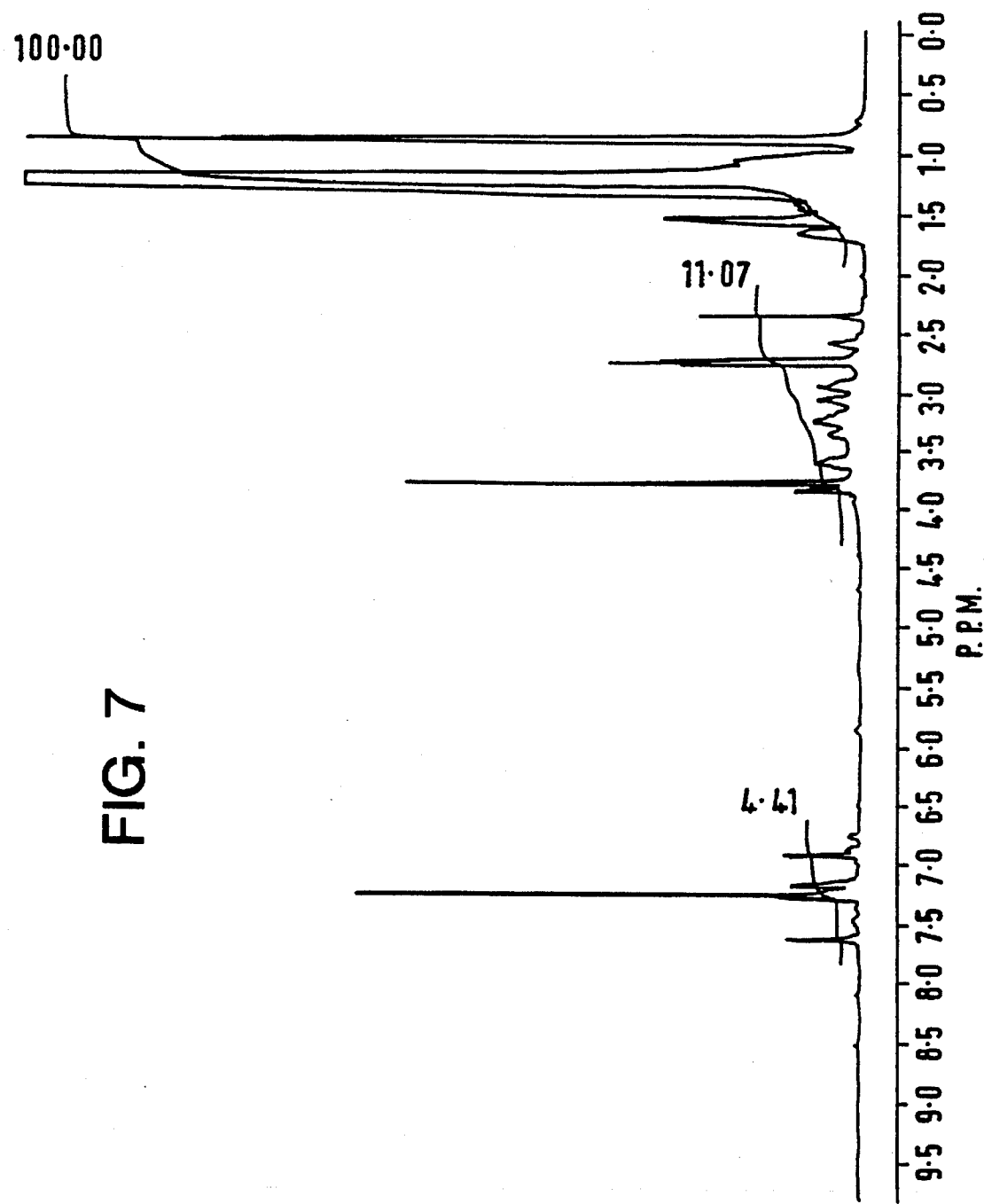

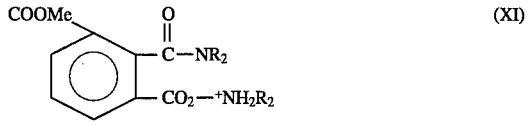

where R is $C_{16/18}$ alkyl, was confirmed by proton NMR spectroscopy and the traces being FIG. 3 hereof.

Further Compounds

Further compounds according to this invention and having the formulae XII, XIII, XIV and XV were made by methods analogous to those described herein.

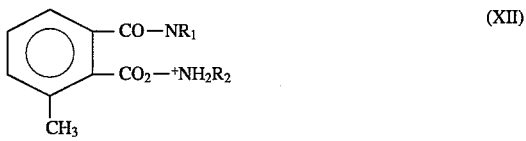

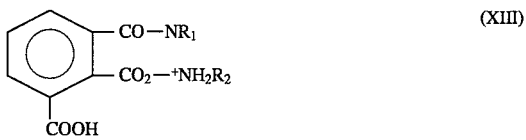

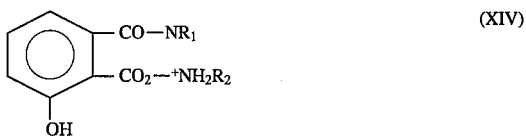

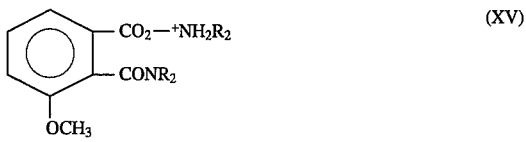

In each of the formulae, R is $C_{16/18}$ alkyl. The structures shown are confirmed by the traces of FIG. 4–7 respectively.

Testing

The effectiveness of Additive A, and additive systems containing it as filterability improvers in distillate fuels were determined by the following methods.

By one method, the response of the oil to the additives was measured by the Cold Filter Plugging Point Test (CFPP) which is carried out by the procedure described in detail in "Journal of the Institute of Petroleum", Volume 52, Number 510, June 1966, pp. 173–285. This test is designed to correlate with the cold flow of a middle distillate in automotive diesels.

In brief, a 40 ml. sample of the oil to be tested is cooled in a bath which is maintained at about −34° C. to give non-linear cooling at about 1° C./min. Periodically (at each one degree C starting from above the cloud point), the cooled oil is tested for its ability to flow through a fine screen in a prescribed time period using a test device which is a pipette to whose lower end is attached an inverted funnel which is positioned below the surface of the oil to be tested. Stretched across the mouth of the funnel is a 350 mesh screen having an area defined by a 12 millimeter diameter. The periodic tests are each initiated by applying a vacuum to the upper end of the pipette whereby oil is drawn through the screen up into the pipette to a mark indicating 20 ml. of oil. After each successful passage, the oil is returned immediately to the CFPP tube. The test is repeated with each one degree drop in temperature until the oil fails to fill the pipette within 60 seconds. This temperature is reported as the CFPP temperature. The difference between the CFPP of an additive free fuel and of the same fuel containing additive is reported as the CFPP depression by the additive. A more effective flow improver gives a greater CFPP depression at the same concentration of additive.

Another determination of flow improver effectiveness is made under conditions of the flow improver Programmed Cooling Test (PCT) which is a slow cooling test designed to indicate whether the wax in the fuel will pass through filters such as are found in heating oil distribution system.

In the test, the cold flow properties of the described fuels containing the additives were determined as follows. 300 ml. of fuel are cooled linearly at 1° C./hour to the test temperature and the temperature then held constant. Wax which has settled in the bottle is dispersed by gentle stirring, then a CFPP filter assembly is inserted. The tap is opened to apply a vacuum of 500 mm. of mercury and closed when 200 ml. of fuel have passed through the filter into the graduated receiver. A PASS is recorded if the 200 ml. are collected within two minutes through a given mesh size of a FAIL if the flow rate is too slow indicating that the filter has become blocked. CFPP filter assemblies with filter screens of 20, 30, 40, 60, 80, 100, 120, 150, 200, 250, 350 and 500 mesh number also 25<m, 20<m, 15<m and 10<m hole size in filter are used, plus a volkswagen tank screen mesh (referred to as VW) and an LTFT filter are used to determine the finest mesh (largest mesh number) the fuel will pass. The larger the mesh number that a wax containing fuel will pass, the smaller are the wax crystals and the greater the effectiveness of the additive flow improver. It should be noted that no two fuels will give exactly the same test results at the same treatment level for the same flow improver additive. The order of the filters used, in increasing pore size is as follows:

10 μm, 15 μm, 20 μm, 25 μm, 500, LTFT, VW, 350, 250, 200, 150, 120, 100, 80, 60, 40, 30, 20 where numbers alone indicate mesh numbers.

EXAMPLE 1

The above additives were tested in the Fuels which had the ASTM D-86 distillation characteristics set out in Table 1.

The wax content is the wt % of wax deposits at 10° C. below the Wax Appearance Temperature.

In the tests 250 ppm of each Additional component were used and the formulations contained varying amounts of either Additive A or Additive G.

The XPCT results give a comparison of the performance of products containing Additive A and Additive G.

The test temperature, the amounts of the various components used and the results are set out in the following table.

| Amount of A or G used (PPM) | Additional Components (250 ppm of each) | Test Fuel | Temp °C. | XPCT results smallest mesh passed A | G |
|---|---|---|---|---|---|
| 0 | | | | VW | VW |
| 50 | | | | LTFT | 500# |
| 125 | B, D + F | 1 | −9° | 25μ | 500# |
| 250 | | | | 15μ | 15μ |
| 500 | | | | 15μ | 15μ |
| 0 | | | | >350# | >350# |
| 50 | | | | >350# | >350# |
| 125 | B + D | 1 | −9° | VW | >350# |
| 250 | | | | 500# | >350# |
| 500 | | | | 10μ | >350# |
| 0 | | | | VW | VW |
| 125 | | | | 20μ | 25μ |
| 250 | B, D + E | 2 | −9° | 20μ | 15μ |
| 500 | | | | 15μ | 15μ |
| 0 | | | | 500# | 500# |
| 125 | | | | 500# | — |
| 250 | B, D + F | 2 | −9° | 20μ | — |
| 500 | | | | 15μ | — |
| 0 | | | | >350# | >350# |
| 125 | | | | VW | 350# |
| 250 | B + D | 2 | −9° | 500# | 500# |
| 500 | | | | 15μ | 15μ |
| 0 | | | | >350# | >350# |
| 125 | | | | VW | 500# |
| 250 | B, D + E | 3 | −12° | 15μ | 20μ |
| 500 | | | | 10μ | 500# |

A dash indicates that a test was not carried out.

TABLE 1

| | Fuel 1 | Fuel 2 | Fuel 3 | Fuel 4 | Fuel 5 | Fuel 6 |
|---|---|---|---|---|---|---|
| Initial Boiling Point | 205° | 148° | 165° C. | 178° | 155° | 145° |
| 5% | 228 | 195 | | 227 | 195 | 195 |
| 10% | 235 | 204 | | 243 | 207 | 207 |
| 20% | 247 | 215 | 245° C. | 261 | 228 | 225 |
| 30% | 258 | 230 | | 272 | 247 | 237 |
| 40% | 269 | 247 | | 282 | 264 | 249 |
| 50% | 279 | 263 | 285° C. | 291 | 277 | 260 |
| 60% | 291 | 279 | | 301 | 289 | 272 |
| 70% | 304 | 297 | | 311 | 302 | 286 |
| 80% | 319 | 315 | | 324 | 316 | 303 |
| 90% | 339 | 339 | 339° C. | 341 | 333 | 329 |
| 95% | 355 | 356 | 352° C. | 355 | 346 | 350 |
| Final Boiling Point | 374° | 373 | 367° C. | 368 | 359 | 367 |
| WAT | 0° C. | 1.0° C. | +10% Kerosene | | −4.7° C. | −6.2° C. |
| C.P. | 2° C. | 2° C. | | | −5° C. | −5° C. |
| Wax Content Below WAT | 2.4% | 3.1% | | | 2.4% | 3.1% |

| Amount of A or G used (PPM) | Additional Components (250 ppm of each) | Fuel | Temp °C. | XPCT results smallest mesh passed | |
|---|---|---|---|---|---|
| | | | | A | G |
| 0 | B | 3 | −12° | >350# | >350# |
| 250 | D E | | | 10μ | 15μ |
| 0 | C | 4 | −9° | >350# | >350# |
| 250 | D E | | | 20μ | 500# |
| 250 | C D E | 4 | −9° | 20μ | 15μ |
| 0 | C | 5 | −15° | >350# | >350# |
| 250 | B E | | | 15μ | 500# |
| 0 | C | 6 | −14° | 80# | 80# |
| 150 | B | | | 20μ | — |
| 250 | E | | | 15μ | 500# |
| 500 | | | | 15μ | 25μ |
| 125 | C | 6 | −19° | VW | — |
| 250 | B | | | 20μ | — |
| 500 | E | | | 15μ | — |
| 125 | E | 6 | −19° | 20μ | — |

A dash indicates that a test was not carried out.

EXAMPLE 2

Various additive combinations were tested in the PCT test by adding the Additive, material below to Fuel 6 containing 50 ppm of an Ethylene/Vinyl acetate copolymer 1 at −14° C. with the following results.

| Additive | Concentration (ppm) | Mesh passed |
|---|---|---|
| A | 50 | 500 |
| A | 125 | 15μ |
| A | 250 | 10μ |
| A | 500 | 10μ |
| H | 250 | 15μ |
| H | 500 | 10μ |
| E | 50 | 500 |
| E | 125 | 15μ |
| E | 250 | 15μ |
| G | 50 | 25μ |
| G | 125 | 500 |
| G | 500 | LTFT |

(under 'Mesh passed', numbers alone indicate mesh size and LTFT is defined as above).

The above results show that the additives of the invention, in the above test, were similar in performance to Additive E and better than Additive G.

EXAMPLE 3

Fuel to which various additive combinations had been added was tested in the XPCT test at −13° C. with the following results, where the fuel had the following characteristics: W.A.T −3.8° C. Cloud Point −3° C. Initial Boiling Point 153° C. Final Boiling Point 373° C. Wax 10° C. below W.A.T=2.2%, XPCT=30 mesh.

| Ethylene/Vinyl Acetate Copolymer | Polyitaconate ($C_{18}$ alkyl) | E | A | Mesh Passed |
|---|---|---|---|---|
| 100 | 100 | 200 | 0 | 500 |
| 100 | 100 | 0 | 200 | 15μ |
| 200 | 0 | 300 | 0 | 20μ |
| 200 | 0 | 0 | 300 | 15μ |

Treat rates of additives are given in ppm (ai).

The results show that, in the tests, additive combinations including A were superior.

EXAMPLE 4

Fuel to which various additive combinations had been added was tested in the XPCT test at −14° C. with the following results, where the fuel had the following characteristics: W.A.T −4° C. Cloud Point −3° C., Initial Boiling Point 140° C., Final Boiling Point 360° C. Wax 10° C. below W.A.T=2.4%, XPCT greater than 30 mesh.

| Ethylene/Vinyl Acetate Copolymer | Polyitaconate ($C_{18}$ alkyl) | E | A | Mesh Passed |
|---|---|---|---|---|
| 200 | 100 | 200 | 0 | 500 |
| 200 | 100 | 0 | 200 | 15μ |

Treat rates of additives are given in ppm (ai).

The results show that, in the tests, the additive combination including A was superior.

We claim:

1. A distillate fuel composition having a boiling point in the range of 120° C. to 500° C. which contains from 0.0001 to 0.5 wt. % of a flow improving additive of the formula

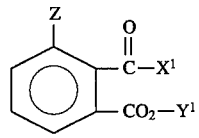

where Z is nitro and $X^1$ and $Y^1$ are the same or different and are selected from the group consisting of $N^{(+)}R^3R^2$, $HN^{(+)}R^3R^2$, $H_2N^{(+)}R^3R^2$, $H_3N^{(+)}R^2$, $N^{(+)}R^3R^1$, $N^{(+)}HR^3R^1$, $H_2N^{(+)}R^3R^1$, $H_3N^{(+)}R^1$, $NR^3R^2$, $—R^2$, $—NR^3R^1$ and $R^1$, $R^1$ and $R^2$ being $C_{10}$–$C_{40}$ alkyl, alkoxy alkyl or polyalkoxyalkyl groups and $R^3$ being a $C_1$–$C_{30}$ alkyl, said additive being effective to reduce the size of wax crystals present in the fuel.

2. The composition of claim 1 wherein the flow improving additive has the formula

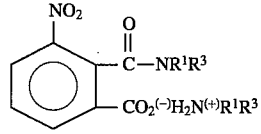

where Z is nitro and $R^1$ and $R^3$ may be $C_{16}$–$C_{18}$ alkyl or $C_{17}$–$C_{18}$ alkyl.

3. The composition of claim 1 wherein $R^1$, $R^2$ and $R^3$ are straight chain alkyl of 18 to 22 carbon atoms.

4. The composition of claim 1 wherein $R^1$, $R^2$ and $R^3$ are branched chain alkyl at the 1 or 2 position and have 18 to 22 carbon atoms.

5. The fuel composition of claim 1 or 2 further comprising at least one other flow improver selected from the group consisting of comb polymers polyoxyalkylene esters, ethers or ester/ethers, ethylene unsaturated ester copolymers and nitrogen-containing polar compounds.

* * * * *

UNITED STATES PATENT AND TRADEMARK OFFICE
CERTIFICATE OF CORRECTION

PATENT NO. : 5,578,091
DATED : November 26, 1996
INVENTOR(S) : Graham Jackson et al.

It is certified that error appears in the above-indentified patent and that said Letters Patent is hereby corrected as shown below:

In column 16, claim 1, line 39, delete "C40" and insert therefore --$C_{40}$--.

In column 16, claim 2, delete the formula

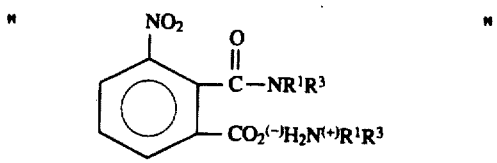

and insert therefore

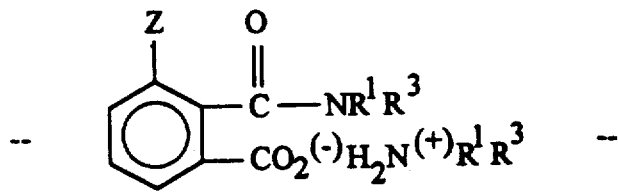

Signed and Sealed this

Thirtieth Day of December, 1997

Attest:

BRUCE LEHMAN

*Attesting Officer*     *Commissioner of Patents and Trademarks*